United States Patent [19]

Hershenson

[11] Patent Number: 4,748,979

[45] Date of Patent: Jun. 7, 1988

[54] PLAQUE RESOLVING DEVICE

[75] Inventor: Harold Hershenson, Coral Gables, Fla.

[73] Assignee: Cordis Corporation, Miami, Fla.

[21] Appl. No.: 37,411

[22] Filed: Apr. 13, 1987

Related U.S. Application Data

[62] Division of Ser. No. 785,108, Oct. 7, 1985, Pat. No. 4,672,962.

[51] Int. Cl.$^4$ .............................................. A61B 17/36
[52] U.S. Cl. .................................. 128/303.1; 128/401
[58] Field of Search ............................................ 128/4–8, 128/200.26, 303.1, 395–403; 604/113, 114

[56] References Cited

U.S. PATENT DOCUMENTS

| | | | |
|---|---|---|---|
| 623,022 | 4/1899 | Johnson | 604/114 |
| 1,677,642 | 7/1928 | Kirk | 604/114 |
| 3,698,394 | 10/1972 | Piper et al. | 128/303.1 |
| 3,798,967 | 3/1974 | Gieles et al. | 128/692 |
| 4,038,519 | 7/1977 | Foucras | 604/114 |
| 4,142,529 | 3/1979 | Latenser et al. | 128/401 |
| 4,207,874 | 6/1980 | Choy | 128/303.1 |
| 4,217,910 | 8/1980 | Khalil | 128/692 |
| 4,224,929 | 9/1980 | Furihata | 128/6 |
| 4,227,535 | 10/1980 | Connor | 128/401 |
| 4,240,441 | 12/1980 | Khalil | 128/700 |
| 4,445,892 | 5/1984 | Hussein et al. | 128/303.1 |
| 4,449,528 | 5/1984 | Auth et al. | 128/303.1 |
| 4,662,368 | 5/1987 | Hussein et al. | 128/398 |

FOREIGN PATENT DOCUMENTS 2315075 12/1974 Fed. Rep. of Germany ... 128/303.1

Primary Examiner—Max Hindenburg
Attorney, Agent, or Firm—Henry W. Collins; Thomas R. Vigil

[57] ABSTRACT

The plaque resolving device is adapted to be inserted into and through the lumen of a blood vessel and manipulatable therethrough to a desired position where the device can be operated to soften atherosclerotic plaque buildup in, and to re-establish desired blood flow through, the blood vessel. The device includes an elongate tubular body having a proximal end, a distal end, and a tip member mounted to the distal end of the tubular body. An electrical heating element is mounted in the tip member for heating the tip member to a desired predetermined temperature. A temperature sensor is also mounted within the tip member. Energy supply and control circuitry is mounted at the proximal end of the tubular body and coupled to the electrical heating element and temperature sensor so that the heating element is maintained at a temperature within a predetermined temperature range relative the ambient temperature of the blood and plaque.

6 Claims, 2 Drawing Sheets

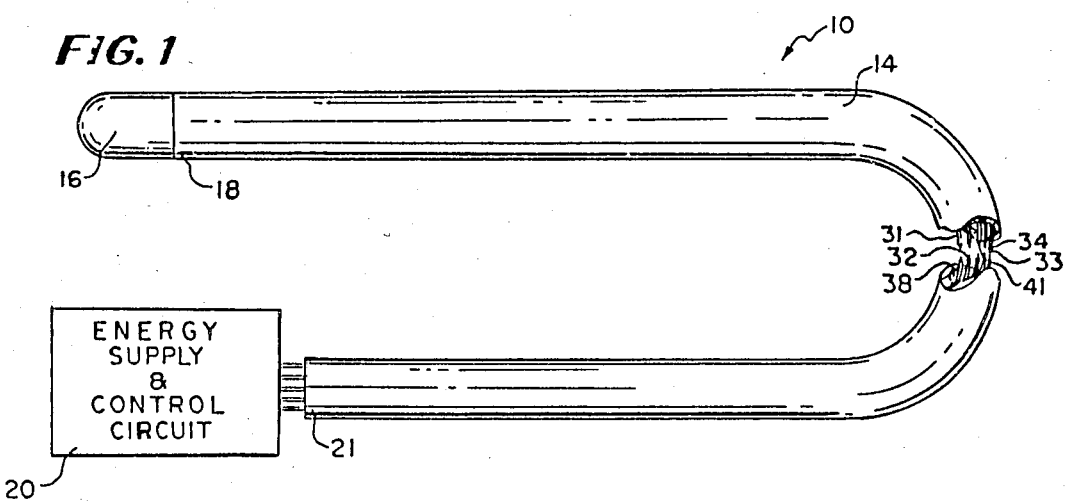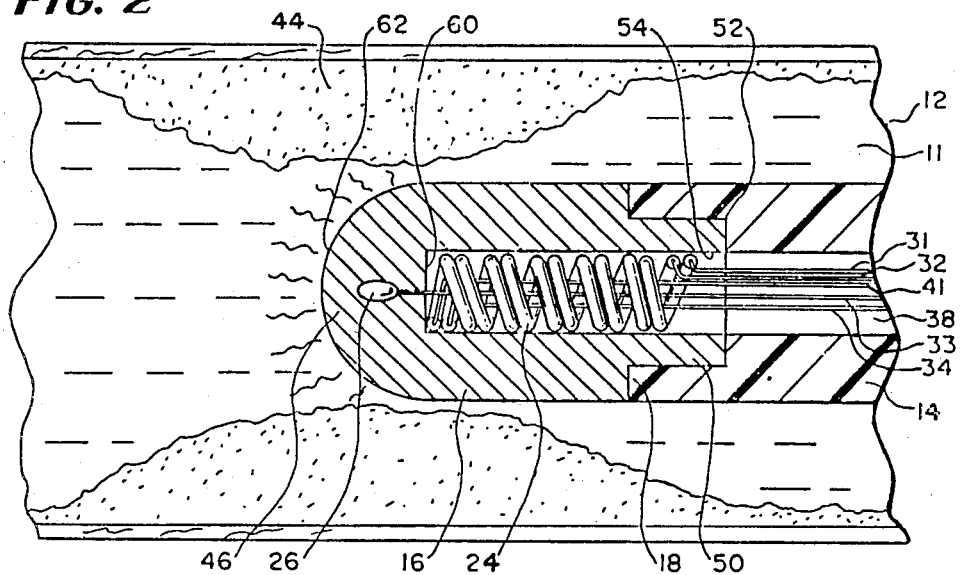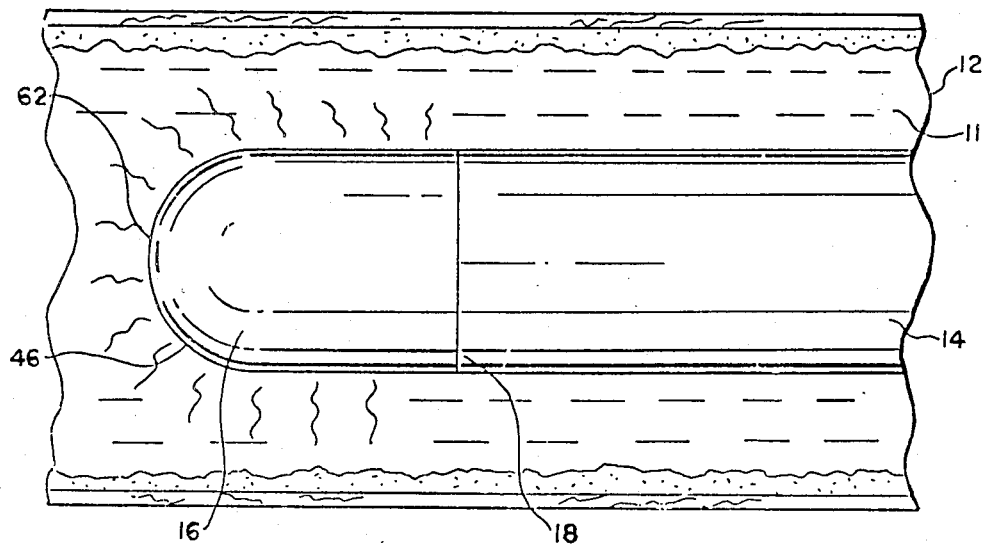

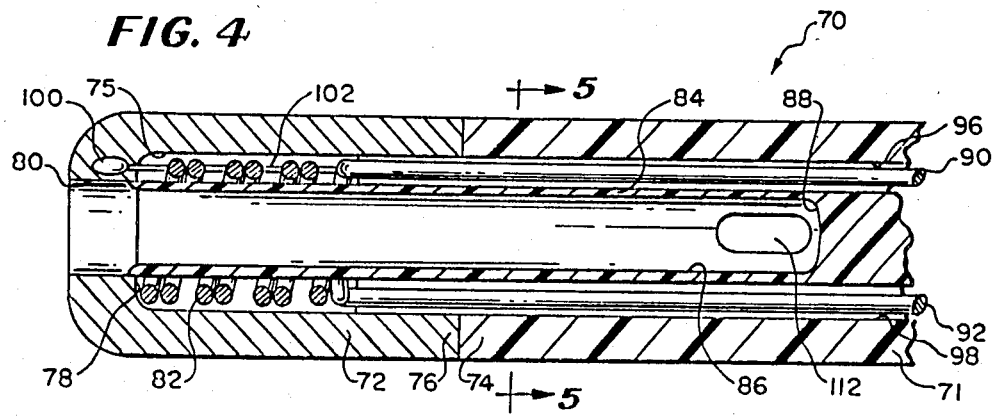
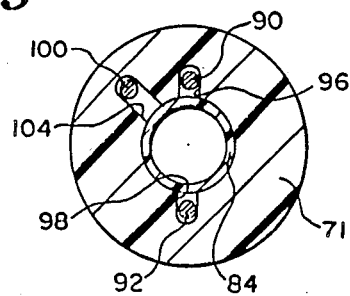

PLAQUE RESOLVING DEVICE

This is a division of application Ser. No. 785,108, filed Oct. 7, 1985, now U.S. Pat. No. 4,672,962.

BACKGROUND OF THE INVENTION

1. FIELD OF THE INVENTION

The present invention relates to a device and method for softening atherosclerotic plaque buildup in a blood vessel in order to restore necessary blood flow. The device includes a catheter with a tip member having heating means therein for applying heat directly to an atherosclerotic plaque area within a blood vessel whereby the heat softens the fatty material of the plaque.

2. DESCRIPTION OF THE PRIOR ART

Heretofore, various body insertable devices with heat generation means, such as a heated tip catheter, have been proposed for delivering heat to internal organs, cavities or vessels of a body.

Such devices have also been used as temperature measuring devices, and for heating fluid transferred to or from the body.

Examples of some of the previously proposed devices are disclosed in the following patents:

| U.S. PAT. NO. | PATENTEE |
|---|---|
| 623,022 | Johnson |
| 1,677,642 | Kirk |
| 3,798,967 | Gieles et al |
| 4,038,519 | Foucras |
| 4,217,910 | Khalil |
| 4,227,535 | Connor |
| 4,240,441 | Khalil |

The Johnson U.S. Pat. No. 623,022 dicloses a catheter which is adapted for insertion into a body cavity and which is allegedly capable of delivering an electric current to the body. The electric current was believed to have some curative powers, and no reference is made in this patent to heat generation. The catheter can be used for delivering fluid into the body and the electric current allegedly flows from the catheter through the fluid into the body.

The Kirk U.S. Pat. No. 1,677,642 discloses a double barrelled catheter wherein one barrel delivers medication and the other barrel delivers heat to any internal cavity, organ or tissue. The barrel which delivers heat is provided with an electrical heater with suitable number of wound conductor turns to provide a desired resistance in conductors which extend through an attaching socket for connection to a source of current.

The Gieles et al U.S. Pat. No. 3,798,967 discloses both a method and a probe for measuring blood flow in a blood vessel. The probe delivers high frequency electromagnetic energy to the blood and this energy is then converted to heat in the blood itself as the blood flows through an energy field formed within a "cage" at the tip of the probe. The heating, however, is indirect in that the probe generates heat in the surrounding blood by creating an electromagnetic field and is only used for flow measuring purposes.

The Foucras U.S. Pat. No. 4,038,519 discloses a flexible heating tube for medical use which is heated by electric resistance wires embedded in the wall of the tube in a helical pattern about the lumen of the tube. The tube is used for the transfer of heated body fluids to and from the body and the heating elements are used to maintain a proper temperature of the fluids.

The Khalil U.S. Pat. Nos. 4,217,910 and 4,240,441 disclose a thermo-dilution catheter having at its distal end a high frequency heating coil, a heat measuring thermocouple and a resistance thermometer which are used for measuring the flow of blood at the catheter distal end in either a jugular vein, a left ventricle, or a carotid artery. The catheter operates on a thermo-dilution principle. In use, the heating coil heats the blood to one temperature at one location and the drop in temperature measured at another location downstream is indicative of the rate of flow of the blood.

The Connor U.S. Pat. No. 4,227,535 discloses a proctological device for therapeutically treating hemorrhoids. The device includes a heating element which is placed in contact with the hemorrhoid to cauterize it. The heating element includes an internal electric resistor within the device for generating heat in response to the application of electrical energy. A temperature transducer is also situated within the device for sensing the temperature of the device in the anal canal. The electrical resistor of the heating element is a helically wound coil on a cylindrical insulative heating core mounted within a cylindrical envelope having an exterior heat transfer surface. The cylindrical envelope has a length sufficient to extend totally from the anus through the anal canal to the rectum.

As will be described in greater detail hereinafter, the device and method for softening atherosclerotic plaques of the present invention differs from the devices and methods previously proposed by providing a catheter which is sized to be received in a blood vessel and which has a heat transfer surface localized in a tip member mounted to the distal end of the catheter. The catheter is manipulatable into and through the lumen of a blood vessel and can be positioned therein proximate atherosclerotic plaque buildup in the blood vessel. Heat is then generated and supplied to the atherosclerotic plaques for a predetermined period of time to resolve the plaque.

Still further, in one preferred embodiment of the present invention, there is provided a tubular tip member open at the distal end and communicating at the proximate end with at least one port in the wall of the device. The tubular tip member and port or ports permit the flow of blood through and around the tip member. The tubular tip member and port permit treatment of plaque buildup for an extended period of time without interrupting the flow of blood through the vessel in the area of the plaque buildup.

SUMMARY OF THE INVENTION

According to the invention, there is provided a plaque softening device adapted to be inserted into and through the lumen of a blood vessel and manipulatable therethrough to a desired position where the device is operated to soften atherosclerotic plaque buildup in the blood vessel to re-establish desired blood flow through the blood vessel, said device comprising: an elongate tubular body having a distal end and a proximate end; a tip member mounted to said distal end of said tubular body; heating means mounted in said tip member for heating said tip member; temperature sensing means mounted in said tip member for sensing the temperature of said tip member; and energy supply and control means coupled to said heating means and to said sensing means for maintaining the temperature of said tip member within a predetermined temperature range relative to the ambient temperature of blood flowing through the blood vessel and of the plaque buildup in the blood vessel.

Preferably the tip member and distal end of the tubular body have passage means for allowing blood to continue to flow around and/or through the tip member while it is maintained proximate to the plaque buildup at an elevated temperature.

BRIEF DESCRIPTION OF THE DRAWINGS

FIG. 1 is a rear view of one embodiment of the plaque softening device of the present invention with a portion of a tubular body of the device broken away to show conductors in a lumen of the tubular body.

FIG. 2 is a fragmentary sectional view of the distal end of one embodiment of the device shown in FIG. 1 and shows a tip member of the device positioned in a blood vessel proximate to an area of surrounding atherosclerotic plaque buildup in the blood vessel.

FIG. 3 is a fragmentary view similar to the fragmentary view shown in FIG. 2 and shows the tip member and a softened area of atherosclerotic plaque buildup within the blood vessel.

FIG. 4 is a fragmentary sectional view of the distal end of another plaque softening device of the present invention.

FIG. 5 is a sectional view taken along line 5—5 of FIG. 4 and shows the location of conductors in a tubular body of the device.

DESCRIPTION OF THE PREFERRED EMBODIMENTS

Referring now to FIG. 1, there is illustrated therein a plaque softening device constructed according to the teaching of the present invention and generally identified by reference numeral 10. According to the teachings of the present invention, the device 10 is adapted to be inserted into and through the lumen 11 of a blood vessel 12 (FIG. 2) and manipulatable therethrough to a position of atherosclerotic plaque buildup.

The device 10 includes an elongate tubular body or catheter 14 made of an insulating material and a metal tip member 16 mounted to the distal end 18 of the elongate tubular body 14. The device 10 further includes an energy and supply control circuit 20 coupled to the proximal end 21 of the tubular body 14. A heating element 24 (FIG. 2) is mounted within the tip member 16 and a temperature sensor 26 for sensing and controlling the temperature of the tip member 16 is also mounted in the tip member 16. The heating element 24 is a double coil element and is coupled by four wire conductors 31-34, that extend through lumen 38 of body 14, to the control circuit 20. Likewise, the sensor 26 is coupled by a wire conductor 41 extending through the lumen 36 to the control circuit 20.

The tubular body 14 is made of a material which is suitable for intravascular use and which provides maximum flexibility so as to permit manipulation of the device 10 through a blood vessel to a desired position therein. The external and internal diameters of the tubular body 14 are sufficient to permit flexibility. Typically the tubular body 14 has a diameter approximately one third (⅓) the diameter of the blood vessel 12 in which it is inserted.

As shown in FIG. 2, the blood vessel 12 has an area 44 of atherosclerotic plaque buildup within or on the lumen or inner wall 11 of the blood vessel 12. The tip member 16 is shown positioned within and surrounded by the area 44 of atherosclerotic plaque buildup.

In this embodiment illustrated in FIG. 2 the tip member 16 has a rounded distal end portion 46 to facilitate insertion of same into and manipulation thereof through the blood vessel 12, and has a boss 50 at its proximal end having the same diameter and length of a mating hollow 52 in the distal end 18 of the tubular body 14 within which the boss 50 is received and fixed to the tubular end 14, such as with an adhesive. The tip member 16 has a bore 54 extending through the boss 50 into the member 16 to a wall 60. The bore 54 is the same diameter as and continuous with the lumen 38 of the tubular body 14.

Mounted within the bore 54 of the tip member 12 is the double coil electrical heating element 24. The conductors 31-34 extend from the lumen 38 of the tubular body 14 into the bore 54 and are connected therein to the element 20. The tip member 16 is made of a heat conducting metal sufficient to transfer heat from the electrical heating element 24 mounted therein to a heating surface 62 of the tip member 16.

As shown the temperature sensor 26 is embedded in the distal end portion 46 of the tip member 16 and connected by the wire conductor 41 to the control circuit 20. Although only one conductor 41 is shown the sensor may actually be coupled by two wire conductors to the control circuit 42. The sensor 26 senses the temperature of the tip member 12 when it is heated by the heating element 24 and supplies a temperature indicating signal via conductor 41 to the external energy and supply control circuit 20.

In using the device 10, after the tip member 16 has been positioned proximate an area 44 of plaque buildup, the tip member 16 is heated to a predetermined temperature of approximately 5° C. to 15° C. and preferably 8° C. above the ambient temperature of the blood for approximately 5 to 15 minutes, preferably 10 minutes. The tip member 16 is positioned proximate to the atherosclerotic plaque buildup area 44 so that the plaque 44 is heated sufficiently to soften the fatty material of which the atherosclerotic plaque area 44 is composed. Once the fatty material is resolved into the blood, it is carried away by the blood through the blood vessel 12. Furthermore, by heating the plaque area 44 with the tip member 16 to a temperature approximately 8° C. above the ambient blood temperature, and maintaining that temperature for approximately 10 minutes, a sufficient amount of plaque will be softened to enable a non-occluded vessel to be established in which blood can flow at a normal rate as shown in FIG. 3.

Another embodiment of the plaque softening device of the present invention is illustrated in FIG. 4 and is generally identified by reference increment 70. The device 70 includes an elongate tubular body 71 and a tubular tip member 72 mounted at the distal end 74 of the tubular body 72.

The tip member 72 has a cylindrical cavity 75 extending from the proximal end 76 of the tip member 72 into the member 72 to a front wall 78 which has a bore 80 therein. A heating coil 82 is received in the cavity 75. As shown an insulating tube 84 extends from the distal end 74 of the body 71 into cavity 75 and into the bore 80 thereby to isolate the coil 82 from another cylindrical cavity 86 within the tube 84.

The cavity 86 extends into the distal end 74 of the tubular body 71 and terminates at an inner end wall 88. If desired the insulating tube 84 with inner end wall 88 can be inserted into a bore in the distal end 74 of tubular body 71 instead of being integral therewith.

The heating coil 82 is coupled to an energy and supply control circuit by first and second conductors 90 and 92, respectively, which extend through elongate slots 96 and 98 in the tubular body 71 as shown.

A temperature sensor 100 is mounted in the front wall 78 as shown and one (or two) conductor(s) 102 extends from the sensor 100 through another elongate slot 104 for connection to the energy supply and control circuit.

In order to facilitate the flow of blood both around and through the tubular tip member 72, at least one port(s) 112 is provided in the side wall of tubular body 71 and through the insulating tube 84 to the cavity 86. The bore 80 of the tip member 72, the cavity 86 and port or ports 112 permit the flow of blood through the tip member 72 so that the flow of blood is not interrupted while the heated tip member 72 is softening plaque.

The tube 84 electrically insulates the blood flowing through the tip member 71 from the heating coil 82.

According to the teachings of the present invention, the method of applying heat to the area of atherosclerotic plaque buildup further includes the introduction of a contrast medium into the blood vessel to determine the amount of plaque reduction after application of heat. The contrast medium is fluoroscopically detectable material which is radiographically monitored by indicating the extent of blood flow through the blood vessel.

Once it has been determined that the atherosclerotic plaque has been softened, the temperature of the heated tip member 16 (FIG. 1) or 72 (FIG. 4) is reduced to a temperature close to the ambient temperature of the blood and removed therefrom.

From the foregoing description, it is apparent that the plaque softening device 10 or 70 of the present invention provides a number of advantages some of which have been described above and others of which are inherent in the invention. In particular, the heated tip member 16 (FIG. 1) or heated tubular tip member 72 (FIG. 4) can be positioned proximate to a particular atherosclerotic plaque area so as to efficiently soften the plaque buildup, and at the same time, permit liquid flow therearound or therethrough.

Also, it will be apparent to those skilled in the art that modifications can be made to the device 10 or 70 of the present invention without departing from the teachings of the present invention. Accordingly, the scope of the invention is only to be limited as necessitated by the accompanying claims.

I claim:

1. A plaque softening device adapted to be inserted into and through the lumen of a blood vessel and manipulatable therethrough to a desired position where said device is operated to soften atherosclerotic plaque buildup in the blood vessel in a process for reestablishing desired blood flow through the blood vessel, said device comprising: an elongate tubular body having a distal end and a proximal end; a tubular tip member mounted to said distal end of said tubular body; heating means mounted in said tip member for heating said tip member; temperature sensing means mounted in said tip member for sensing the temperature of said tip member; energy supply and control means coupled to said heating means and to said sensing means for maintaining the temperature of said tip member within a predetermined temperature range relative to the ambient temperature of blood flowing through the blood vessel and of the plaque buildup in the blood vessel, said tubular tip member and said tubular body having means for facilitating liquid flow therethrough including an opening at the distal end of said tubular tip member which communicates through said tip member with at least one port in a wall of said tubular body adjacent said tip member to permit flow of blood through the vasicular area of plaque buildup while such area is being heated by said tip member, said tip member having a cylindrical cavity therein and said heating means including a heating coil mounted within said cylindrical cavity; and an insulating tube extending from said tubular body into and through said cylindrical cavity to said opening to isolate said heating coil from blood flowing through said insulating tube between said opening and said at least one port.

2. The device of claim 1 wherein said heating and/or said sensing means mounted in said tip member are coupled to said energy supply and control means by wire conductors extending through said tubular body.

3. The device of claim 1 wherein said heating coil and said sensing means are mounted in said tubular tip member and are coupled to said energy supply and control means by conductors extending in internal elongate slots in said tubular body adjacent but outwardly of said insulating tube.

4. The device of claim 1 wherein said insulating tube insulates said heating coil and said sensing means from the lumen within said insulating tube through which blood flows.

5. The device of claim 1 wherein said elongate tubular body is a catheter.

6. A plaque heating device adapted to be inserted into and through the lumen of a blood vessel and then manipulated therein to a desired position where said device is operated to heat atherosclerotic plaque buildup in the blood vessel, said device comprising: an elongate tubular body having a distal end and a proximal end; a heat conductive tip member mounted to said distal end of said tubular body and having a distal end and a proximal end; heating means mounted in said tip member for heating said tip member; temperature sensing means mounted in said tip member for sensing the temperature of said tip member, said tip member having passage means therethrough from a point at or adjacent said distal end of said tip member to a point at or adjacent said proximal end of said tip member; said tubular body having at least one opening in a side wall thereof adjacent the proximal end of said tip member and communicating with said passage means in said tip member; and insulating means extending from said opening and through most of said passage means for isolating said heating means and most of said tip members from blood flowing through said passage means between said opening in said tubular body and said distal end of said tip member.

* * * * *